US00PP13732P3

(12) United States Plant Patent
Yoshida et al.

(10) Patent No.: US PP13,732 P3
(45) Date of Patent: Apr. 22, 2003

(54) APPLE TREE 'KITARO'

(75) Inventors: Yoshio Yoshida, Ebetsu (JP); Shichiro Tsuchiya, Ryugasaki (JP); Junichi Soejima, Morioka (JP); Tadayuki Haniuda, Nagano (JP); Tetsuro Sanada, Morioka (JP); Yoshiki Kashimura, Tsukuba (JP); Tetsuo Masuda, Morioka (JP); Hideo Bessho, Yamanashi-ken (JP); Sadao Komori, Ishigaki (JP); Yuji Ito, Ibaraki-ken (JP); Kazuyuki Abe, Morioka (JP); Nobuhiro Kotoda, Morioka (JP)

(73) Assignee: National Agricultural Research Organization, Tsukuba (JP)

( * ) Notice: Subject to any disclaimer, the term of this patent is extended or adjusted under 35 U.S.C. 154(b) by 0 days.

(21) Appl. No.: 09/270,841

(22) Filed: Mar. 18, 1999

(65) Prior Publication Data

US 2002/0002716 P1 Jan. 3, 2002

(51) Int. Cl.[7] ..... A01H 5/00
(52) U.S. Cl. ..... Plt./172
(58) Field of Search ..... Plt./172

(56) References Cited

PUBLICATIONS

Soejima et al., Breeding of Fuji Apples and Performance on JM Rootstocks; Compact Fruit Tree; vol. 31 (1); pp. 22–24; 1998.*

GTITM UPOVROM Citation for 'Ringo Morioka 52 Go' as per JP PBR 9766; Apr. 11, 1997.*

Kaju Syubyo, vol. 68 (1997), pp. 24–25, Explanation of a new registered variety by The MAFF ② Apple Variety 'Kitaro' (in Japanese with English translation).

Compact Fruit Tree, vol. 31, No. 1, Jan. 1998, Breeding of Fuji and Performance on JM Rootstocks by The International Dwarf Fruit Tree Association (in English).

* cited by examiner

*Primary Examiner*—Kent Bell
(74) *Attorney, Agent, or Firm*—Armstrong, Westerman & Hattori, LLP

(57) ABSTRACT

Disclosed is an apple tree having a medium vigor, rounded and crenated leaves, exhibiting excellent resistance to Alternaria blotch and bearing a medium size fruit maturing mid-season and having high productivity with an slightly heavy preharvest fruit drop. The fruit has an oblate shape, has yellow colored skin and has excellent storage quality. The flesh of the fruit is yellowish white, juicy and firm, and further, has a strong sweetness and medium sourness, thereby providing a good sweet-sour balance and rich taste, and has an excellent eating quality.

8 Drawing Sheets

BACKGROUND OF THE VARIETY

The present invention relates to a new and distinctive variety of apple tree belonging to a medium-maturing apple cultivar and, more particularly, relates to an apple variety having high quality and high resistance to disease and insect, for eating raw and for processing.

Regarding medium-maturing apple varieties, although 'Jonathan' and 'Starking Delicious' were widely cultivated in the past, they have become unpopular due to their taste and poor storage quality, and there are no main medium-maturing apple varieties now known to us. Thus it was necessary to breed a main medium-maturing apple variety immediately.

Accordingly, the present breeders crossed 'Hatsuaki', which is an excellent variety for both eating raw and for processing, with 'Fuji', which is a main economical variety, to obtain excellent medium-maturing apple varieties having good fruit quality and high productivity. Namely, the purpose of the invention is to avoid russet on fruit surface and to improve the storage quality of the medium-maturing variety 'Hatsuaki' and to breed a new and distinct variety of medium-maturing apple variety having excellent disease and insect resistance for eating raw and for processing.

ORIGIN AND ASEXUAL REPRODUCTION OF THE VARIETY

To accomplish this purpose, the breeders crossed 'Fuji', which had been cultivated at the Morioka branch of the Fruit Tree Research Station (currently the Apple Research Center, the National Institute of Fruit Tree Science), in Japan, and 'Hatsuaki' in 1976 and obtained seeds. The seeds obtained were utilized for sowing and raising seedlings at said branch, in 1977, and the resulting seedlings were then grafted on 'M27', the most dwarfing rootstock, to accelerate bearing in 1978, and 127 individuals were set in 1980.

The trees bore fruit in 1984 and one was selected in the primary selection as a good medium-maturing individual in 1986. The present invention is directed to an apple tree 'Kitaro', which is one individual from among the 127 individuals derived from the cross 'Fuji' (♀) (the seed parent) and 'Hatsuaki' (♂) (the pollen parent), and was given an individual number "512" during testing. Then the tree was selected as a favorable line of trees, which have a line name Ringo Morioka 52 Go, have been provided for local adaptability tests since 1991, and were examined to determine the various characteristics thereof, over a period of eight years from April 1989 to March 1997. As a result, it was found that, for example, fruit of the trees had the desired characteristics, such as quality, storage quality and yield, as a medium-maturing apple variety, and the tree was distinguishable from the parent varieties, 'Fuji' and 'Hatsuaki', as well as a control variety 'Golden Delicious'. Accordingly, the breeders denominated this variety as 'Kitaro', in accordance with this invention. The genus and species of the tree is '*Malus×domestica*'.

Of the varieties, 'Fuji' is a variety generated from a cross between 'Ralls Janet' and 'Delicious'.

Of the varieties, 'Hatsuaki' is a variety generated from a cross between 'Jonathan' and 'Golden Delicious'.

The breeders asexually reproduced this new and distinctive variety of apple tree 'Kitaro', by grafting on rootstock 'M.27' (U.S. Plant Pat. No. 3,793), at a number of Fruit Tree Research Stations in Morioka City, Iwate prefecture, Japan, and confirmed the homogeneity and stability of 'Kitaro' according to the present invention. The instant plant retains its distinctive characteristics and reproduces true to type in successive generations.

Of the above varieties, only M.27 is known to us as having been patented in the United States.

An application for this new variety of apple tree, 'Kitaro' under the Seeds and Seedlings Law of Japan, was filed on Apr. 11, 1997, under the filing number 9766.

The original tree of this apple tree is held at the Apple Research Center of the National Institute of Fruit Tree Science, Ministry of Agriculture, Forestry and Fisheries, residing at 92 Nabeyashiki, Shimokuriyagawa, Morioka City, Japan.

SUMMARY OF THE VARIETY

This new variety of apple tree, having medium vigor, is spreading, and many spurs and axillary buds are formed.

The leaves of the tree are elliptic and serrated.

At Morioka City, Iwate prefecture, Japan, the trees have a flowering time around May 21th. As the type of S gene of the present variety is (S3, S9), the cross-compatibility with common cultivars except 'Hatsuaki' and 'Sekaiichi' is high.

There is slightly heavy preharvest drop of fruit and the present variety exhibits high productivity. Regarding the main diseases, the tree is resistant to Alternaria blotch, but is susceptible to scab. It has not been recognized so far that any disease or insect except for the above, is significant.

The ripening of the present fruit occurs in mid October at Morioka, later by about one week than 'Senshu', and earlier by one week than 'Golden Delicious'. The size of the fruit is medium and averages about 250–270 g, the same as 'Senshu'. Although the type of ground color of the skin of the fruit is yellow (6D by RHS) and that of the over-color is red-purple (63C by RHS), the surface of the skin, receiving sunlight is colored with dull pink. The shape of the fruit is oblate and the amount of the russet on the skin is high, thus the appearance of the fruit is not good. Depending on the years, cracking occurs in the stalk cavity of the fruit.

The flesh of the present fruit contains much sugar, about 15–16% Brix of the total sugar, and about 0.5 g/100 ml of malic acid, and further the flesh is firm and juicy, has a strong sweetness and medium sourness and provides a good sweet-sour balance and rich taste. The storage quality of the fruit is excellent, and is about 15 days at room condition and more than 90 days in cold storage.

Compared with the seed parent, 'Fuji', the present variety is distinguishable in that ripening of the fruit is earlier by about 20 days than that of 'Fuji', the type of over color of the skin of the present variety is yellow, whereas that of 'Fuji' is colored with deep-reddish stripe, and the fruit of the present variety does not have tendency to an inclination of the axis, as does 'Fuji'.

Compared with the pollen parent, 'Hatsuaki', the present variety is distinguishable in that flowering is earlier by several days and the ripening of the fruit is later by about 10–15 days than that of 'Hatsuaki', the color of the skin is yellow, whereas that of 'Hatsuaki' is reddish-orange, and the flesh of the present variety is firm, and the storage quality is excellent.

Compared with 'Golden Delicious', the present variety is clearly distinguishable in that the ripening of the fruit is earlier by about one week, and there is preharvest drop of the fruit, the shape of the fruit is flatter than that of 'Golden Delicious', the flesh is firm and the storage quality is excellent.

The color references presented are herein taken from The Royal Horticultural Society Color Chart (R.H.S.) except where general terms of ordinary significance are used.

DESCRIPTION OF THE VARIETY

Figure 1:
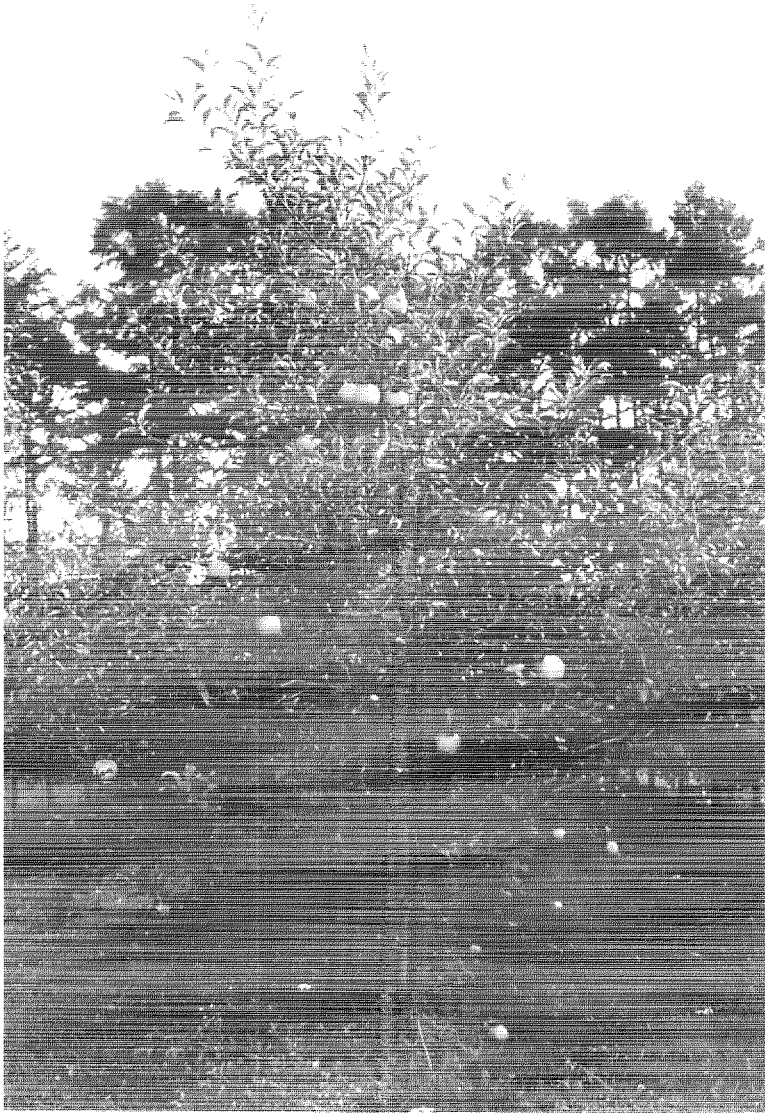
FIG. 1 is a photograph of a tree shape of the new variety of apple tree grafted on 'M.9' (8 years old)
Figure 2:
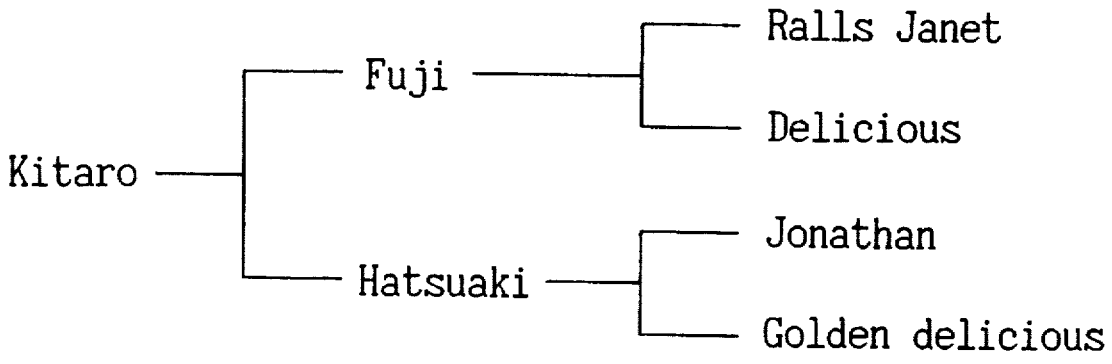
FIG. 2 gives the pedigree of the new and distinct variety of the apple tree 'Kitaro'.
Figure 3:
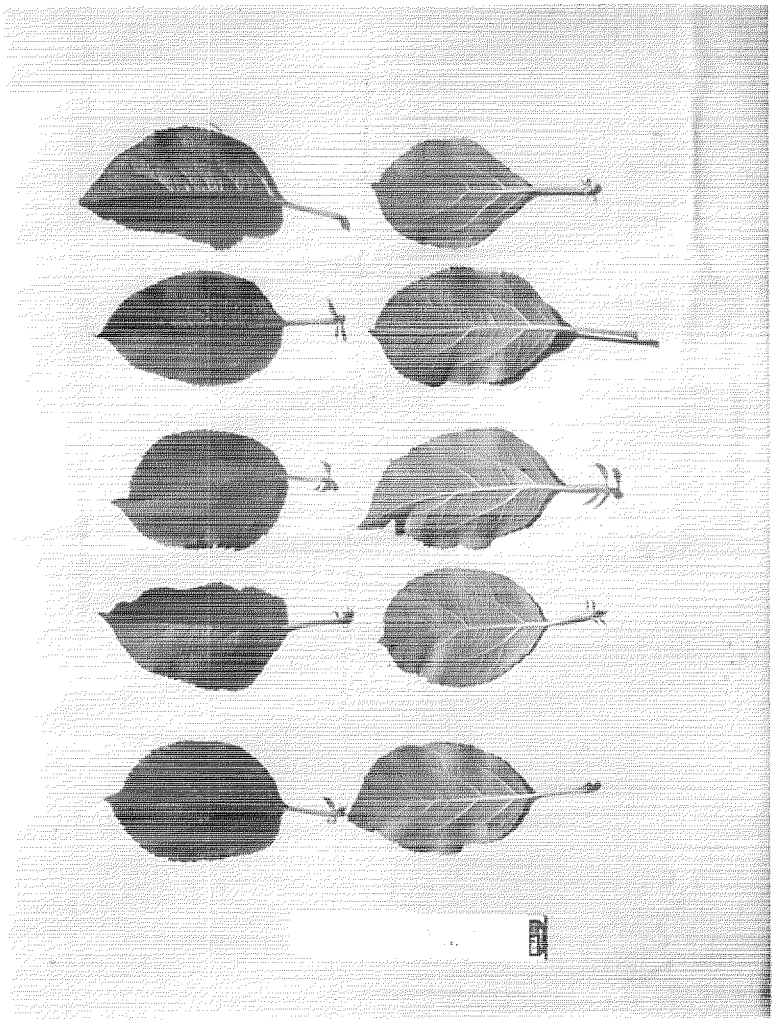
FIG. 3 is a photograph of adult leaves (upper and under side) of the new variety of apple tree.
Figure 4:
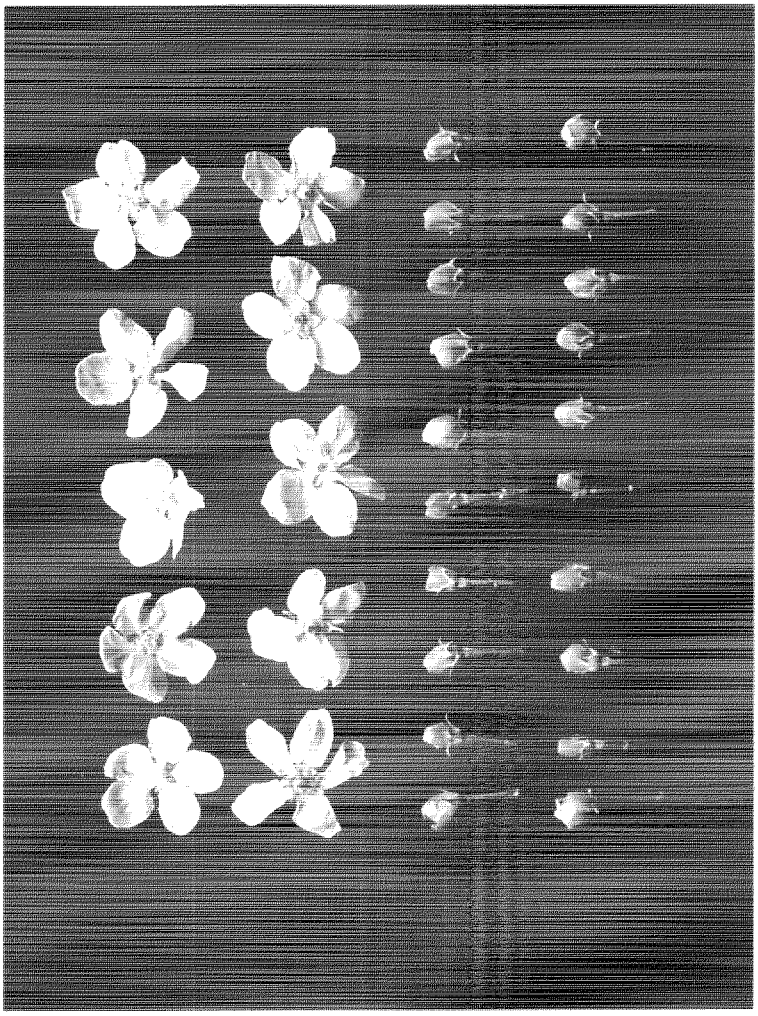
FIG. 4 is a photograph of the flowers (opened and unopened) of the new variety of apple trees.
Figure 5:
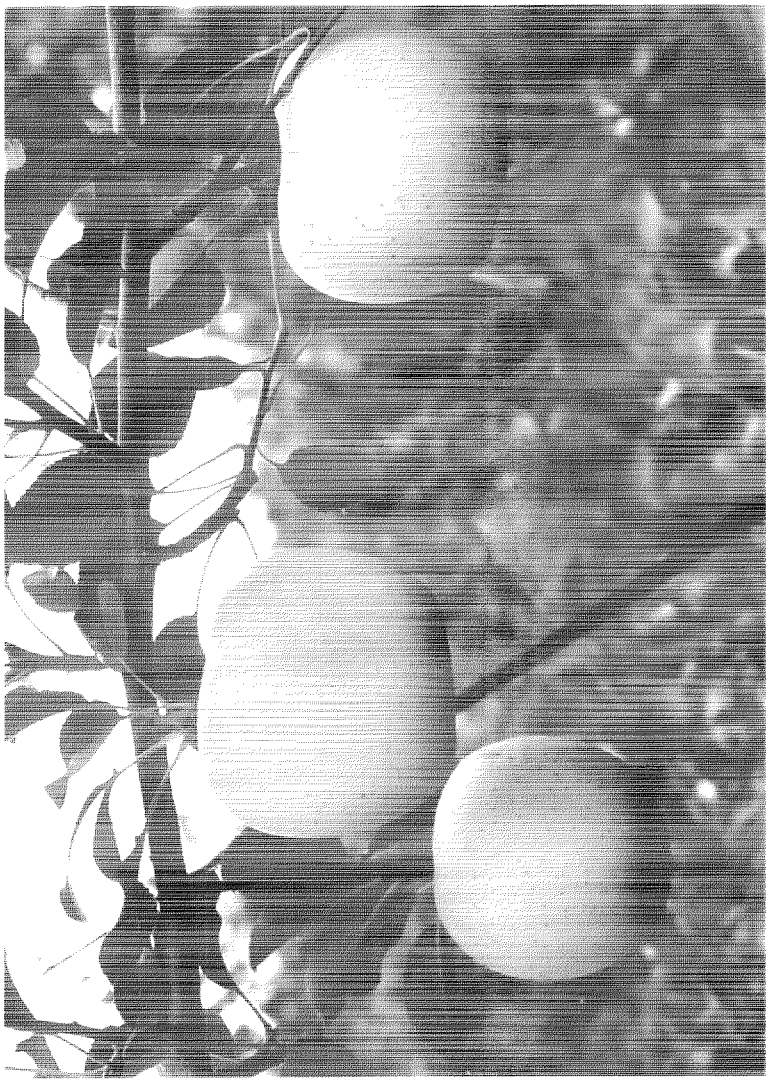
FIG. 5 is a photograph of the fruit on the tree of the new variety of apple tree.
Figure 6:
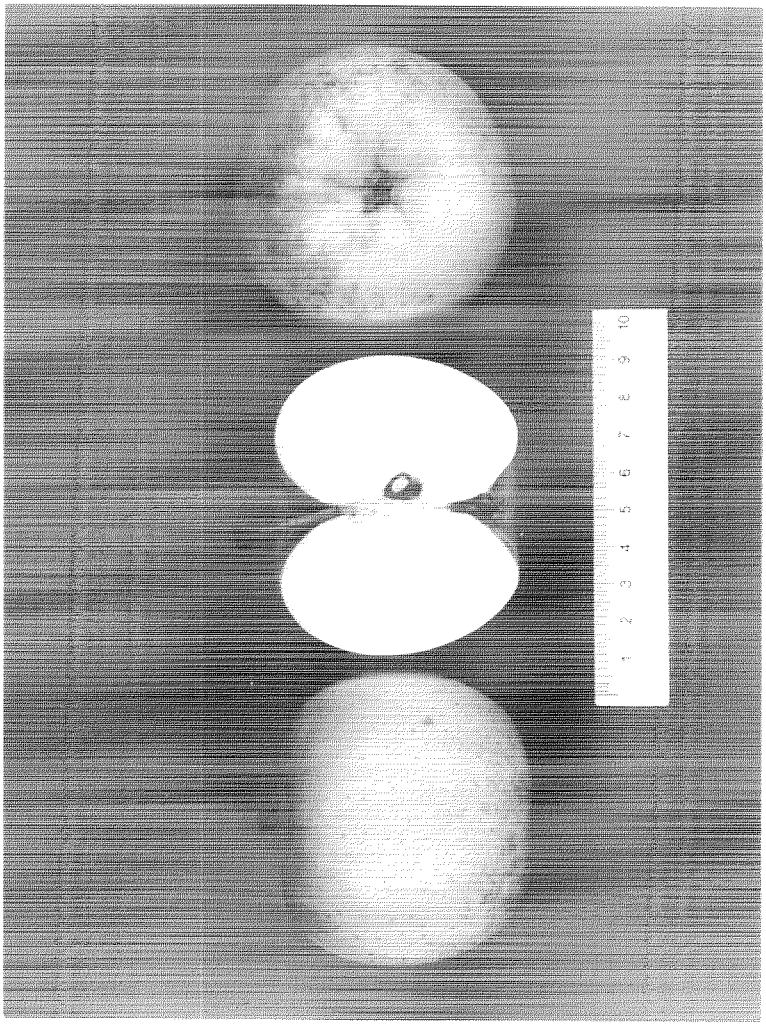
FIG. 6 is a photograph of a side view, longitudinal-sectional view, and basin of the fruit of the new variety of apple tree.
Figure 7:
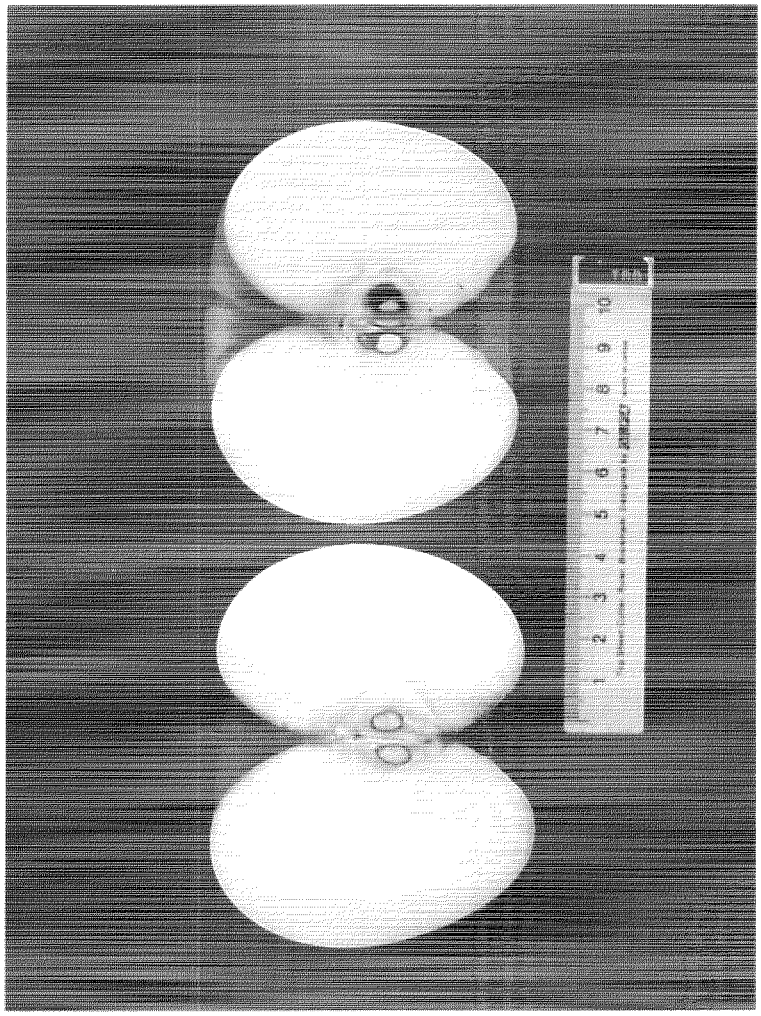
FIG. 7 is a photograph of a longitudinal-sectional view of the fruit of the new variety of apple tree.
Figure 8:
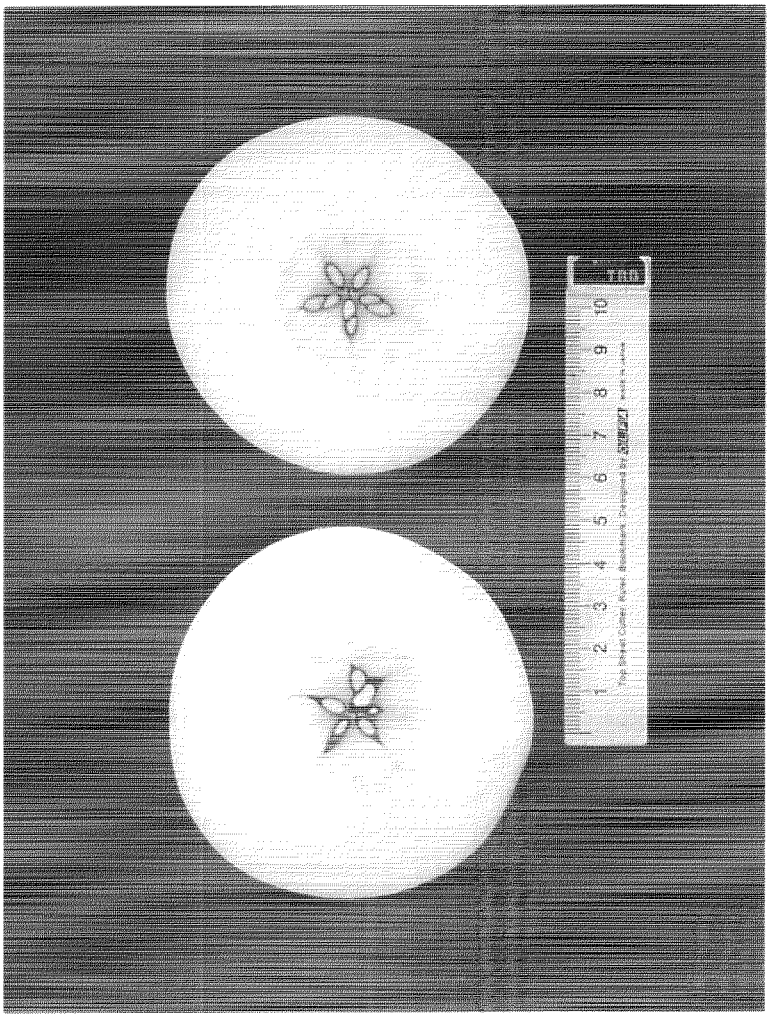
FIG. 8 is a photograph of a cross-sectional view of the fruit of the new variety of apple tree.

The characteristics of the new and distinct variety of apple tree Kitaro are as follows (10-year-old tree investigated in Morioka City, Iwate prefecture, Japan):

Tree:

*Tree height.*—361 cm (atypical, as top of tree was cut to make tree easier to work with.

*Tree diameter.*—3.76 m. Trunk diameter (30 cm above soil level): 9.7 cm.

*Bark coloration.*—Gray-brown (199D).

*Crotch angles.*—67.3°.

*Texture of branch.*—Slightly rough.

*Coloration of branch.*—Gray-brown (199D).

*Habit of branches.*—Medium and spreading, same as 'Golden Delicious'.

*Length of four-year-old branch.*—166 cm.

*Diameter of middle of four-year-old branch.*—12.9 mm.

*Length of one-year-old shoot.*—40.0 cm.

*Diameter of one-year-old shoot.*—4.0 mm.

*Time to produce a fruit-bearing tree.*—4 years in Morioka City, Iwate prefecture, Japan.

*Length of internode (one-year-old shoot).*—Short (average 2.8 cm).

*Size of lenticels (one-year-old shoot).*—Length 1.60 mm, width 0.60 mm.

*Number of lenticels (one-year-old shoot).*—11.7/cm$^2$ (numerous).

*Pubescence of shoot.*—Sparse.

*Bearing habit of fruit.*—On spur. Number of axillary flower bud: about 3.5/shoot.

Leaf:

*Shape of leaf blade.*—Elliptic, whereas that of 'Golden Delicious' is between rounded and long.

*Margin.*—Serrated.

*Size of leaf (length).*—Short (length average 8.4 cm, wide average 5.2 cm).

*Color of leaf.*—Upper surface green (133A) and under surface green (138C).

*Leaf apex.*—Acuminate.

*Leaf base.*—Cuneate.

*Venation pattern.*—Venose.

*Shape of stipules.*—Sickle.

*Size of stipules.*—Short (length 10.8 mm, width 2.2 mm).

*Color of stipules.*—Upper surface green (133A), under surface green (138C).

*Size of petiole.*—Medium (length 25.5 mm, diameter 1.8 mm).

*Color of petiole.*—Yellow-green (150D).

Flowers:

*Number of flowers (per cluster).*—Medium (4–6).

*Size (open flower).*—Medium (diameter 51 mm).

*Color (unopen flower).*—Red-purple (65B).

*Shape of flower bud.*—Ovoid.

*Size of flower bud.*—Length 12.6 mm, diameter 8.8 mm.

*Color of flower bud.*—Red-purple (58C–65C).

*Shape of petal.*—Ovoid, whereas that of 'Golden Delicious' is oval.

*Number of petals.*—Medium (5).

*Size of petals.*—Length 26.2 mm, width 18.0 mm.

*Shape of petals.*—Apex obtuse, base mucronate.

*Margin of petals.*—Entire.

*Texture of petals.*—Soft.

*Color of petals.*—Upper surface white (155D–69D), under surface red-purple (63D–65D).

*Number of stamens.*—Medium.

*Color of anthers.*—Light yellow.

*Amount of pollen.*—Much.

*Color of pollen.*—Yellow (7A).

*Number of sepals.*—5.

*Size of sepals.*—Length 9.5 mm, width 3.9 mm.

*Shape of sepals.*—Sharp pointed, apex acute (bases of sepals are linked together).

*Color of sepals.*—Upper surface green (139D), under surface green (138D).

Fruit:

*Size.*—Length 69.7 mm, diameter 86.3 mm.

*Shape.*—Oblate, whereas that of 'Golden Delicious' is short-round conical.

*Crowing at eye end.*—Medium, that of 'Golden Delicious' is weak.

*Aperture of eye.*—Open.

*Depth of basin (eye end).*—Medium, (12 mm), that of 'Golden Delicious' is deep.

*Diameter of basin (eye end).*—Broad (38 mm), that of 'Golden Delicious' is narrow.

*Depth of stalk cavity.*—Medium (18 mm), same as 'Golden Delicious'.

*Diameter of stalk cavity.*—Broad (34 mm), whereas that of 'Golden Delicious' is medium.

*Size.*—Small (about 250–270 g).

*Type of ground color.*—Yellow (6D), whereas that of 'Golden Delicious' is light yellow.

*Type of over color of skin.*—Red-purple (63C), whereas that of 'Golden Delicious' is light yellow.

*Amount of over color of skin.*—5–10%.

*Form of over color of skin.*—Solid (undistinguished stripe).

*Position of russet.*—Overall.

*Amount of russet.*—Less than 5–10%.

*Raised russet lenticels.*—Present.

*Size of lenticels.*—Medium (diameter 1.3 mm), whereas that of 'Golden Delicious' is large.

*Number of lenticels.*—Medium (2.3/cm$^2$).

*Silvery mottle of skin.*—Absent.

*Luster of skin color.*—Not shiny.

*Greasiness of skin.*—Medium, more than 'Golden Delicious' but less than 'Jonagold' when touched with the hand.

*Bloom of skin.*—Absent.

*Cracking tendency of skin.*—The skin has a tendency to crack, whereas that of 'Golden Delicious' does not.

*Surface texture of skin.*—Rough, rougher than 'Golden Delicious'.

*Length of stalk.*—Medium (about 3.0 cm).

*Diameter of stalk.*—2.4 mm.

*Distinct swelling at end of stalk.*—None.

*Shape of core.*—Conical.

*Size of core.*—Small, (length 31.0 mm, diameter 30.3 mm).

*Number of core cells.*—Medium (5 core cells) (loculus).

*Color of flesh.*—Yellow (11D).

*Bruising of flesh.*—Difficult, whereas that of 'Golden Delicious' is easy.

*Browning of flesh.*—Strong, stronger than that of 'Golden Delicious'.

*Firmness of flesh.*—Firm, firmer than that of 'Golden Delicious'.

*Texture of flesh.*—Coarse, coarser than that of 'Golden Delicious'.

*Water core.*—None or weak.

*Sweetness of flesh.*—Strong (Brix 15–16%), sweeter than 'Golden Delicious'.

*Acidity of flesh.*—Medium (about 0.5 g/100 ml).

*Astringency of flesh.*—None.

*Flavor of flesh.*—Similar to that of 'Fuji'. Juiciness of flesh: Juicy.

Seed:

*Total number of seeds.*—7.0 per apple.

*Number of fully developed seeds.*—7.0 per apple.

*Number of perfect seeds.*—7.0 per apple.

*Shape.*—Ovoid.

*Size.*—Large (length 9.6 mm, width 5.8 mm).

*Color.*—Gray-orange (166A).

Physiological and ecological characteristics:

*Date of germination.*—Late (around April 10$^{th}$ in Morioka City, Iwate prefecture, Japan), later than that of 'Golden Delicious'.

*Season of flowering.*—Late (first day of bloom May 16th, day of full bloom is around May 21st, and last day of bloom is May 25th, in Morioka City, Iwate prefecture, Japan), later than that of 'Golden Delicious'.

*Time of fruit harvest.*—Medium (first day October 9th, peak period around October 13 to 19th, and last day October 20th in Morioka City, Iwate prefecture, Japan), earlier than that of 'Golden Delicious'.

*Amount of fruit harvest.*—24.2 Kg per plant.

*Time of fructification.*—Precocious.

*Self-fruitfulness.*—0%. (Fructification by self-pollination).

*Early dropping of fruit.*—None or slight.

*Preharvest dropping of fruit.*—Heavy.

*Physiological disorder of fruit.*—Medium, cracking on part of the stalk cavity. Storage quality of fruit (room condition): Long (about 15 days). Storage quality of fruit (cold storage): Very long (about 90 days). Occurrence of heart rot (core rot): None or weak. Resistance to Alternaria blotch: Strong; stronger than 'Golden Delicious'.

Culture: As the preharvest drop of the fruit of the new cultivar is slightly heavy, it is necessary to pay attention to optimum picking time and to avoid late picking.

What is claimed is:

1. A new and distinct cultivar of Apple plant, as illustrated and described.

* * * * *

Pedigree of 'Kitaro'